United States Patent [19]

Dorner et al.

[11] 4,061,538

[45] Dec. 6, 1977

[54] ENZYMATICALLY OXIDIZING INTERFERON

[75] Inventors: Friedrich Dorner, Vienna; Marianne Scriba, Maria Enzerdorf; Rudolf Weil, Vienna, all of Austria

[73] Assignee: Sandoz Ltd., Basel, Switzerland

[21] Appl. No.: 547,782

[22] Filed: Feb. 6, 1975

Related U.S. Application Data

[63] Continuation-in-part of Ser. No. 456,702, April 1, 1974, abandoned.

[30] Foreign Application Priority Data

Apr. 4, 1973 Switzerland ........................ 4801/73
Apr. 4, 1973 Switzerland ........................ 4802/73

[51] Int. Cl.$^2$ ....................... C12D 13/06; C07B 29/02

[52] U.S. Cl. ....................... 195/29; 424/85; 424/177; 260/112 R

[58] Field of Search ................. 195/29, 28 N; 424/85, 424/177

[56] References Cited

U.S. PATENT DOCUMENTS 3,548,053  12/1970  Joshi ..................................... 424/85

*Primary Examiner*—Alvin E. Tanenholtz
*Attorney, Agent, or Firm*—Gerald D. Sharkin; Robert S. Honor; Thomas O. McGovern

[57] ABSTRACT

The invention provides structurally modified interferons, processes for producing such and a method of purification of interferons and structurally modified interferons. The modified interferons are useful as antiviral agents.

3 Claims, No Drawings

ENZYMATICALLY OXIDIZING INTERFERON

This application is a continuation in part of our copending application Ser. No. 456,702, filed Apr. 1, 1974 and now abandoned.

This invention relates to interferons, in particular to the purification and structural modification thereof.

Interferons are known, anti-virally active compounds which are produced in vivo by living organisms and in vitro by tissue cultures in response to the action of a variety of specific inducers, in particular both viral and non-viral inducers. They are well described in the literature and have been shown to have a broad spectrum of activity against many different types of viruses, to be non-toxic and to be non-antigenic. Interferons, therefore, have great potential in the treatment and, in particular, prophylaxis of viral infections, especially having regard to the rather limited range of the synthetic, anti-viral drugs currently available. However, their potential has not been realised due to the inability to produce interferons in sufficient quantity, the lack of purity of the interferons hitherto produced, and the fact that interferons have a relatively short half-life when administered parenterally.

The present invention provides a number of methods of modifying the interferon structure such that the half-life is increased while the anit-viral activity is not substantially diminished. The present invention also provides a method of purifying interferons and structurally modified interferons.

Little is known about the chemical nature of interferons, largely because of the insufficient purity of interferons hitherto produced, thus ruling out direct chemical analysis. Some structural characteristics have, however, been deduced by various enzymatic and chemical treatments of impure interferon preparations and evaluation of anti-viral activity of the resulting products. What is clear is that interferons are proteins, or at least contain protein as a main component, and that part of the molecule consists of carbohydrate radicals. It has also been tentatively suggested that interferons are glycoproteins having a terminal sialic acid unit [E. Schonne et. al., Symp. Series Immunobiol. Standard 14, 61 (1969)] although this hypothesis has yet to be conclusively confirmed. The present invention is based on, and largely supports, the assumption that interferons are such glycoproteins. The present invention also confirms that the penultimate saccharide unit is a galactose radical.

The present invention provides processes for producing interferon derivatives characterised by
a. enzymatically introducing sialic acids into interferons or asialointerferons using specific sialyl transferases,
b. enzymatically oxidising the terminal galactose unit in asialointerferons with galactose oxidase,
c. enzymatically splitting the terminal galactose unit in asialointerferons with specific galactosidase.

Process (a) may be effected employing methods conventional for the introduction of sialic acids, particularly N-acetylneuraminic acid, into glycoproteins or asialoglycoproteins. The specific sialyl transferases employed are also known for such processes and include sialyl transferase from rat liver (RLST) [J. Hickman et. al., J. Biol. Chem. 245, 759 (1970)], from cattle colustrum (CCST) [B.A. Bartholomew and G.W. Jourden, Methods in Enzymology 8, 368 (1966)], from sheep submaxillary gland (SSGST) [D.M. Carlson et. al., Methods of Enzymology, 8, 361 (1966)] and from embryonic chicken brain (ECBST) [B. Kaufman and S. Basu, Methods in Enzymology 8, 365 (1966)]. The conditions at which the process is preferably carried out are standard and vary depending on the enzyme employed. Thus, in general the process is effected in a pH range of from 5.5 to 8.0 although this varies with the enzyme employed. Thus, with RLST, which is the preferred transferase, the pH is preferably 6.0 to 8.0, using, for example, 2-(N-morpholino) ethane sulphonic acid or Tris-chloride buffers; with CCST the pH is preferably 6.4 to 7.2, using, for example, phosphate buffers, and with SSGST, the pH is preferably 5.8 to 6, using Cacodylate acetate buffer. There are no demonstrable metal requirements for these enzymes, although EDTA may stimulate the activities. The sialic acid donor is suitably CMP-N-acetylneuraminic acid, but may alternatively by CMP-N-glycolylneuraminic acid where SSGST is employed as the transferase. Temperatures and other conditions are conventional and are described in the literature.

Process (b) is also carried out in manner conventional for the oxidation of terminal galactose residues in glycoproteins using the enzyme galactose oxidase (which is available commercially). The conditions of the oxidation are standard and it may, for example, be effected at a pH of from 7.0 to 8.0 using, for example, a phosphate buffer. The degree of oxidation may be checked by subsequent reduction of the newly formed C6 aldehyde group with labelled, e.g., tritiated, sodium borohydride. When the reduced material is hydrolysed, e.g. with hydrochloric acid, the resulting labelled galactose in the hydrolysate can be determined by paper chromatography.

Process (c) is effected in standard manner for splitting off terminal galactose units in glycoproteins, using β-galactosidases known for this purpose, including those of bacterial or animal origin, e.g. that from *Dipplococcus pneumoniae* (DPG) [R.C. Hughes and R.W. Jeanloz, Biochem. 3, 1535 (1964)], from *Concanavalia ensiformis* (CEG) [Y.T. Li and S.C. Li, Methods in Enzymology 28, 702 (1972)], from *Phaseus vulgaris* (PVG) [K.M.L. Agranal and O.P. Bahl, Methods in Enzymology 28, 720 (1972)], from *Aspergillus niger* (ANG) [O.P. Bahl and K.M.L. Agranal, Methods in Enzymology 28, 728 (1972)] and from *Clostridium perfringens* (CPG) [E.J. McGuire et. al., Methods in Enzymology 28, 755, (1972). The conditions of the process are conventional and depend largely on the enzyme employed. Thus, for example, while the process may generally be effected at a pH of from 3.5 to 6.5, the preferred pH ranges for specific enzymes are, with DPG, which is most preferred, 6.3 to 6.5 using, for example, phosphate buffer, with CEG, 3.5 to 4.5; with PVG, 3.5 to 4.8, and with ANG 3.8 to 4.6 and with CPG 4.5 to 8.0. The splitting off of the galactose residues can be ascertained with tritiated asialointerferon. This is treated with β-galactosidase, dialysed and hydrolysed, and the tritiated galactose can be detected in the hydrolysate.

The resulting interferon derivatives can be concentrated and purified in conventional manner, for example by ultra-centrifugation, electrofocusing or chromatography.

The asialointerferons, which are interferons in which terminal sialic residues have been released fully or partially, used as starting materials in processes (a), (b) and (c), are either known [E. Schonne et al. Symp. Series Immunobiol. Standard 14, 61(1969)] or can be produced in manner conventional for removing terminal sialic acid residues from glycoproteins. They may thus be produced by mild acid hydrolysis of interferons, for example by prolonged incubation at pH 2 in the cold, for example at 4° C for 1 week. Alternatively, they may be produced by treatment of interferons with neuraminidase of bacterial or animal origin, for example that obtained from *Vibrio cholerae, Clostridium perfringens* or *Diplococcus pneumoniae* [R. Drzenieck, Current Topics in Microbiology and Immunology 59, 35(1972)] or from rat heart. The incubation conditions are standard and depend on the neurominidase employed. For example, with V. chloerae neuraminidase a pH of 5.5 seems to be optimum, using for example acetate buffer, and with D. Pneumoniae a pH of 6.5 is preferable.

If desired, the alternative desialyation procedures described above can both be effected to obtain increased desialyation.

The resulting asialointerferons can be isolated and purified using conventional techniques.

The interferons themselves, used as starting materials, are well described in the literature and may be produced by interaction of inducers, such as RNS- and DNS- viruses, as well as non-viral inducers, such as natural or synthetic double strain RNS with cells, in vivo or in vitro. Specific interferons that may be mentioned are interferons induced by various inducers in the rabbit, chick, mouse, ape, calf, pig, duck or man.

The present invention also provides a process for the production of structurally modified interferons biosynthetically by incomplete synthesis of the carbohydrate portion of interferons. More particularly, the invention provides a method of producing a structurally modified interferon comprising inhibiting carbohydrate synthesis during interferon biosynthesis by incorporating specific inhibitors, which preferably contain 2-desoxyglucose or 2-desoxy-2-aminoglucose, into the reaction medium. The process is carried out in manner conventional for the inhibition of carbohydrate synthesis in proteins. For example, employing 2-desoxyglucose or 2-desoxy-2-aminoglucose, the process is suitably carried out at a temperature of about 30° to 40° C, preferably 37° C. The resulting product is modified to the extent that it appears to contain no terminal galactose units.

The structurally modified interferons so produced may be isolated and purified by conventional techniques.

The invention also provides a purification process for preparation of interferons, asialointerferons or interferons modified in accordance with the invention, comprising chromatographing the preparation over an immobilised agglutinin and subsequently desorbing the agglutinin-bound interferon, asialointerferon or modified interferon. This affinity chromatographic purification procedure can be carried out in conventional manner. Thus, the agglutinin ligand is suitably immobilised in a substantially inert solid matrix. Suitable matrixes depend to some extent in the agglutinin employed, but the preferred matrix is agerose which is activated in known manner and covalently binds to the agglutinin (e.g. P. Cuatrecasas et al. Biochemistry 11, 2291-2299). The interferons are specifically adsorbed through their carbohydrate portions to the agglutinin while impurities largely pass through. The adsorbed interferons are then eluted with a suitable eluant. Suitable agglutinins are those which can be used for known glycoprotein purification, particularly phytohaemaglutinins from *Lens culinaris, Triticum vulgaris, Lotus tetragonolobus, Ricinus comunis* and preferably *Phaseus vulgaris*. The eluant used to desorb the bound interferon may depend on the agglutinin employed but, in general, is suitably a mono-, oligo- or polysaccharide, or another glycoprotein, preferably a glycoprotein or fragment thereof obtained from human erythrocytes [S. Kornfeldt et al., Proc. Nat. Acad. Sci. (USA) 63, 1439–1446]. The interferons may also be desorbed by adjusting the pH to a value of 2.

The modified interferons of the invention possess similar anti-viral properties to unmodified interferons but their half-lives are longer. In particular, they are active against the *Herpes simplex* virus as indicated in white New Zealand rabbits (1.0–2.0 kg) injected with $10^3$ pfu *Herpes simplex* virus. 3 to 6 days after administration, all the rabbits develop increasing paralysis and in approximately two thirds of the rabbits, encephalites with normally lethal results sets in. $10^6$ units of the interferon preparation are injected as a single dose or in 4 divided doses at 6 hourly intervals, beginning at the onset of infection and the results in the animals observed.

For the above-mentioned use, the dosage will, of course, vary depending on the compound employed, mode of administration and therapy desired. However, in general, satisfactory results are obtained when administered at a daily dosage $10^5$ to $10^7$ units per Kg animal body weight, preferably given as a single dose or in divided doses 2 to 4 times daily. For the larger mammals, the total daily dosage is in the range of $5.10^6$ to $200.10^6$ units. Unit dosage forms suitably comprise from about $10^6$ to $50.10^6$ units of the compounds admixed with a suitable liquid pharmaceutical diluent, for parenteral administration. e.g. intravenous administration in the form of sterile injectable solutions or suspensions.

The subject-matter of the references quoted in the foregoing description is hereby incorporated by reference.

The following Examples illustrate the invention. In the Examples, reference is made to isoelectric focusing. This is carried out as an LKB 7900 Uniphor Column Electrophoresis system, Volume 220 ml, using pH 3-10 ampholine carrier ampholytes. The isoelectric focusing is performed according to the LKB Instruction Manual. All operations are carried out at 2° C. After 36 hours, 5 ml fractions are collected and the pH immediately recorded.

EXAMPLE 1

PRODUCTION OF INTERFERON

Interferon is produced in primary rabbit kidney cells according to the method of Tan et. al., Proc. Nat. Acad. Sci. 67, 464–471 with the following modification. Monolayers are incubated with 200 µg/ml of poly(1) poly(C) for 1 hour at 37° C. After removing the inducer the cells are washed twice with Hanks buffered saline solution and 10 µg/ml of cycloheximide in Eagle's minimum essential medium containing 2% fetal calf serum is added. The cultures are incubated for 3½ hours at 37° C, then 3 µg/ml of actinomycin D is added and the incubation continued for a further ½ hour. The antimetabolities are removed, the cells washed 5 times with Hanks solution and covered with freshmedium without serum. After 8 to 10 hours, the supernates are harvested, centrifuged and stored at −70° C unitl use.

20 liters of supernate are concentrated 200 fold by ultra filtration through Diaflo PM-10 membranes (Amicon), dialysed against dilute acetic acid (pH 3.0) and freed from precipitated proteins by centrifugation.

For interferon assays, the plaque reduction test on primary rabbit kidney cells is used. Monolayers in 6 cm Petri dishes are treated for about 18 hours with 2 ml of interferon dilutions and then challenged with 50 to 80 plague forming units of Vesicular stomatitis virus. Titers are expressed as the interferon dilution causing a 50% plaque reduction. An international standard is included in each series of assays. All results are corrected to this standard and expressed as international units per 2 ml.

scribed by S. Kornfeld el al., Proc. Nat. Acad. Sci. (USA) 63, 1439–1446.

After the addition of this glycoprotein fragment to the eluant, a sharp maximum is obtained (see the graph). All the remaining radioactivity is eluted, i.e. the interferon is desorbed within a sharply limited range.

Graph

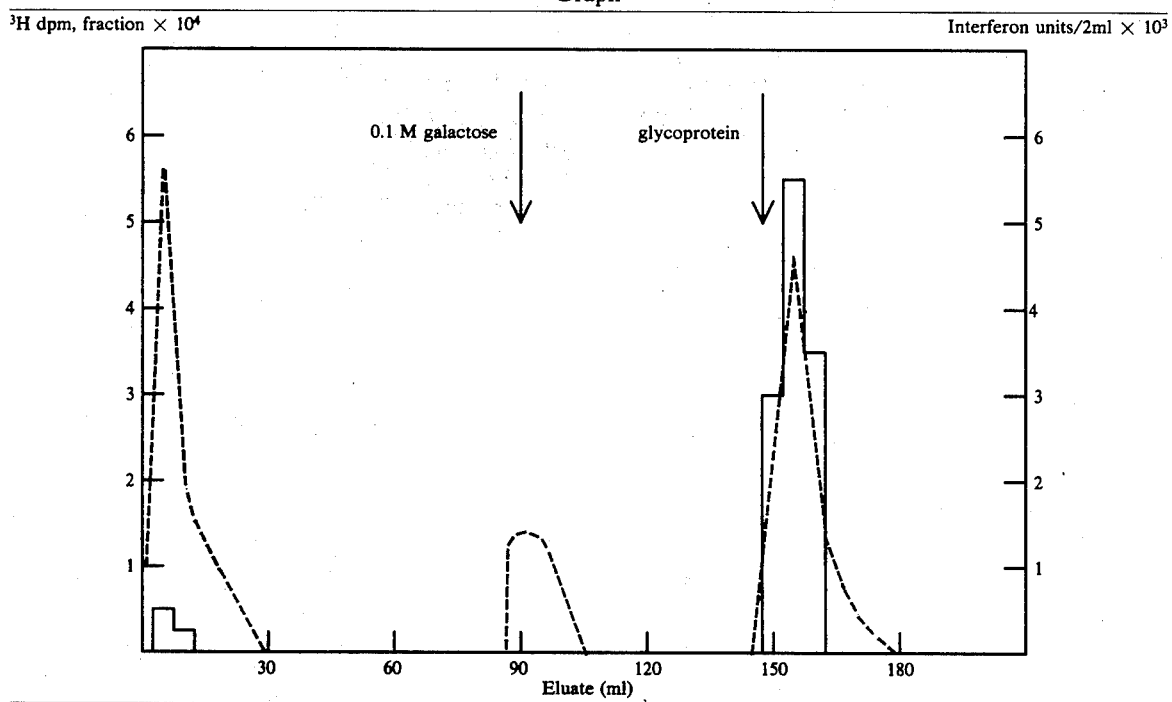

EXAMPLE 2
PURIFICATION PROCESS

The phytoagglutinin of *Phaseolus vulgaris* required for the process is present as bactophytemmagglutinin and is purified as described by T. Weber et al., Scand. J. Hamat. 4, 77–80. The erythroagglutinating portion is gel-filtered on Sephadex G-150 and then coupled with the N-hydroxysuccinimide ester of the succinylated aminoalkyl agarose (P. Cuatrecasas et al., Biochemistry 11, 2291–2299).

This agglutinin shows a specific reaction with the oligosaccharide sequence galactose →N-acetyl-glucosamine →mannose, which is present in many glycoproteins as structural characteristic. As may be seen in the graph, [$^3$H]-marked asialointerferon adsorbs very strongly on this lectin coupled with agarose.

A total amount of 10,000 units of interferon with 120,000 dpm [$^3$H] activity is used. Approximately 50% of the radioactivity do not adsorb, a further 20% can be eluted with 0.1 M galactose. However, this material showed no biologic activity. A complete desorption is obtained with a glycoprotein fragment from human erythrocytes. This glycoprotein fragment is obtained from the membrane of human erythrocytes after treatment with trypsin in accordance with the method de-

EXAMPLE 3
BUILDING IN OF N-ACETYL-NEURAMINIC ACID INTO INTERFERON

Reagents: CMP-N-acetyl-neuraminic acid is synthesised from CTP-N-acetyl-neuraminic acid with the enzyme CMP-sialylic acid transferase from salivary glands [E.L. Kean et al., Methods in Enzymology, 8, 208 (1966)]. The enzyme sialyl transferase is obtained from rat liver [J. Hickman et al., J. Biol, Chem. 245, 759 (1970)] or cattle colostrum [B.A. Bartholomew et al., Methods in Enzymology, 8, 368 (1966)].

4 cc of a solution of rabbit interferon containing $2.10^6$ units of interferon in 0.05 M tris HCl buffer, pH 7.5, 10 millimols of EDTA, 5 millimols of magnesium acetate, are incubated with 2 millimols of CMP-N-acetyl-neuraminic acid and 500 units of sialyl transferase. After two hours the solution is dialyzed against 0.1 N acetic acid and then against distilled water, and the precipitate is removed by centrifuging. The supernatant material contains interferon into which N-acetyl-neuraminic acid is additionally built in.

The enzymatic transfer is verified by isoelectric focusing. Whereas before the treatment interferon is present in several molecular species of pI 6.3; 5.8; 5.3, the newly resulting product mainly has a pI of 4.8. The building in is further confirmed by the transfer of radioactive N-acetyl-neuraminic acid. When CMP-[$^{14}$C]-N-acetyl-neuraminic acid is used in the enzymatic reaction, the pI 4.8 fraction shows a high building in of [$^{14}$C] activity proceeding from marked neuraminic acid. The modified interferon is active against the virus Herpes Simplex in rabbits at a daily dosage of $10^6$ units.

EXAMPLE 4

ENZYMATIC OXIDATION OF ASIALOINTERFERON

A solution of 40 cc of rabbit interferon with $5.10^6$ units of interferon is treated in 0.05 M sodium acetate buffer, pH 5.5, 0.15 M NaCl, 20 millimols of $CaCl_2$, with an international unit of neuraminidase of bacterial or animal origin. After 4 hours the material is dialyzed against 0.1 N acetic acid and subsequently against water. Asialointerferon is present in the supernatant material. When such a preparation is subjected to isoelectric focalization, it may be seen, as has already been described (E. Schonne et al., Symp. Series immunobiol. Standard. 14, 61–68), that the heterogeneity of charge has disappeared and a uniform product with a pI of 6.3 has been formed. This asialointerferon is oxidized with the enzyme galactose oxidase. $2.10^6$ units of interferon in 0.05 M sodium phosphate buffer, pH 7.8, 0.05 M NaCl, are incubated with 500 units of galactose oxidase for 20 hours. After dialysis against 0.1 N acetic acid, centrifuging is effected.

The reaction is ascertained by reduction of the newly formed C6 aldehyde group of the terminal galactose with tritated $NaBH_4$. When the reduced material is electrofocalized, the pI 6.3 interferon fraction shows a high building in of tritium. This material is hydroyzed in 2N HCl for 2 hours at 100° C, is neutralized with $Ag_2CO_3$ and freed from ions with an ion exchange resin. Tritium-marked galactose may be detected unobjectionably in the hydrolyzed material by paper chromatrography (see Table). This Table shows results obtained with untreated and treated interferon and asialointerferon.

Table

| Reduction with $NaB[^3H_4]$ | Incubation with galactose oxidase | Total [$^3$H] building in dpm/μg protein | [$^3$H] building in galactose dpm/μg protein |
|---|---|---|---|
| Interferon | − | 39.115 | 2.182 |
| Interferon | + | 24.765 | 6.224 |
| Asialointerferon | − | 26.593 | 4.080 |
| Asialointerferon | + | 113.135 | 77.724 |

The modified interferon of this Example is active against the virus Herpes Simplex in rabbits at a daily dosage of $10^6$ units.

EXAMPLE 5

SPLITTING OFF OF TERMINAL GALACTOSE $10^7$ Units of rabbit asialointerferon in 0.01 M sodium phosphate buffer, pH 6.5, are incubated with 1000 units of β-galactosidase from Diplococcus pneumoniae, [R.C. Hughes and R.W. Jeanloz, Biochem. 3, 1535 (1964)], for 3 hours. Dialysis is then effected against 0.1 N acetic acid and the precipitate is removed by centrifuging. The supernatant material contains agalactointerferon. The splitting off of galactose may be ascertained with tritated asialointerferon. When this material is treated with β-galactosidase, is plentifully dialyzed and subsequently subjected to acid hydrolysis, no tritated galactose can be detected in the hydrolyzed material.

The modified interferon of this Example is active against the virus Herpes simplex in rabbits at a daily dosage of $10^6$ units.

EXAMPLE 6

BIOSYNTHESIS OF MODIFIED INTERFERON

Interferon is induced in primary-rabbit kidney cells with 200 γ/ml Poly 1:C. After incubation for 60 minutes, the inducer is filtered off, the cells washed three times and mixed with a fresh medium containing 40mM 2-desoxyglucose or 40mM 2-desoxyaminoglucose. After incubation for 10 hours at 37° C, the interferon in the supernate is recovered.

The recovered material is subjected to isoelectric focusing and material with biological activity is found only in the pH range 6.3 to 6.8, whereas natural interferon bands in various ranges. The product is shown to contain no terminal galactose residues in the following manner. $10^6$ units of the biosynthetically modified interferon is incubated, as in Example 3, in 0.05M Tris HCl buffer (pH 7.5), 10mM EDTA, 5mM magnesium acetate with 2mM CMP-N-acetylneuraminic acid and 500 units of sialyl transferase. In contrast to asialointerferon, the biosynthetically modified interferon does not take up any N-acetylneuraminic acid. The molecular species with pI 6.3 to 6.8 remains thus after treatment with sialyl transferase and no additional fractions with lower pI values appear. The fact that, in accordance with Example 3, sialic acid residues are transferred to terminal galactose residues, demonstrates that the biosynthetically modified interferons contain no terminal galactodse residues as acceptors for sialic acid.

The modified interferon of this example is active against the virus Herpes Simplex in rabbits at a dosage of $10^6$ units.

EXAMPLE 7

Similar results to those obtained in Examples 2 to 6 may be obtained using other animal interferons, for example monkey interferon, calf interferon and human interferon.

What is claimed is:

1. A process for the production of a structurally modified interferon, comprising enzymatically oxidising the terminal galactose unit in asialointerferon with galactose oxidase and recovering the modified interferon.

2. A process according to claim 1, in which the oxidation is effected at a pH of from 7.0 to 8.0.

3. A process according to claim 2, in which the pH of the reaction medium is controlled with phosphate buffer.